(12) United States Patent
Nishimoto et al.

(10) Patent No.: US 10,799,213 B2
(45) Date of Patent: Oct. 13, 2020

(54) ULTRASOUND PROBE, ELEMENT CIRCUIT THEREOF, AND ULTRASOUND DIAGNOSTIC DEVICE USING SAME

(71) Applicant: Hitachi, Ltd., Chiyoda-ku, Tokyo (JP)

(72) Inventors: Takuma Nishimoto, Tokyo (JP); Yutaka Igarashi, Tokyo (JP); Toru Yazaki, Tokyo (JP); Kengo Imagawa, Tokyo (JP); Yusaku Katsube, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1163 days.

(21) Appl. No.: 15/102,542

(22) PCT Filed: Nov. 28, 2014

(86) PCT No.: PCT/JP2014/081586
§ 371 (c)(1),
(2) Date: Jun. 8, 2016

(87) PCT Pub. No.: WO2015/093259
PCT Pub. Date: Jun. 25, 2015

(65) Prior Publication Data
US 2016/0310104 A1    Oct. 27, 2016

(30) Foreign Application Priority Data

Dec. 19, 2013  (JP) .................................. 2013-262585

(51) Int. Cl.
*A61B 8/00* (2006.01)
*A61B 8/14* (2006.01)
(Continued)

(52) U.S. Cl.
CPC .......... *A61B 8/4488* (2013.01); *A61B 8/4444* (2013.01); *A61B 8/4494* (2013.01);
(Continued)

(58) Field of Classification Search
CPC ............... G10K 11/346; G01S 15/8925; G01S 15/8927; B06B 1/0215; B06B 1/0622; B06B 2201/76; A61B 8/14; A61B 8/4405
See application file for complete search history.

(56) References Cited

U.S. PATENT DOCUMENTS 4,837,754 A * 6/1989 Nakagawa .......... G01S 7/52046
367/103
5,132,939 A    7/1992 Conrad
(Continued)

FOREIGN PATENT DOCUMENTS

JP    5-184570 A    7/1993
JP    2000-316848 A    11/2000
(Continued)

OTHER PUBLICATIONS

International Search Report (PCT/ISA/210) issued in PCT Application No. PCT/JP2014/081586 dated Feb. 24, 2015 with English translation (5 pages).
(Continued)

*Primary Examiner* — Boniface N Nganga
(74) *Attorney, Agent, or Firm* — Crowell & Moring LLP (57) ABSTRACT

Provided are an ultrasound probe, an element circuit thereof, and an ultrasound diagnostic device, whereby high image quality is possible and reduced size and lower cost are made possible. Provided is an ultrasound probe, comprising: a 2-D array transducer wherein a plurality of transducers are arrayed two-dimensionally; and a 2-D array IC in which are formed, upon an IC substrate, drive circuits which are disposed upon each of the transducers of the 2-D array transducer to drive each of the transducers at different timings with a prescribed delay quantity, and common current sources which supply drive current to the transducers of the 2-D array transducer. The number n of the common current sources which are formed upon the IC substrate is fewer than the number N of the drive circuits which are formed upon the IC substrate.

8 Claims, 7 Drawing Sheets

(51) Int. Cl.
  *B06B 1/06* (2006.01)
  *G01S 15/89* (2006.01)
  *B06B 1/02* (2006.01)
  *G10K 11/34* (2006.01)

(52) U.S. Cl.
  CPC .......... *B06B 1/0215* (2013.01); *B06B 1/0622* (2013.01); *G01S 15/8925* (2013.01); *G01S 15/8927* (2013.01); *G10K 11/346* (2013.01); *A61B 8/14* (2013.01); *A61B 8/4405* (2013.01); *B06B 2201/76* (2013.01)

(56) References Cited

U.S. PATENT DOCUMENTS

| | | |
|---|---|---|
| 2006/0264747 A1 | 11/2006 | Freeman et al. |
| 2012/0294113 A1 | 11/2012 | Amemiya |
| 2013/0226005 A1 | 8/2013 | Kano |

FOREIGN PATENT DOCUMENTS

| | | | |
|---|---|---|---|
| JP | 2001-8934 A | 1/2001 | |
| JP | 2004-8535 A | 1/2004 | |
| JP | 2007-503242 A | 2/2007 | |
| JP | 2008-289780 A | 12/2008 | |
| JP | 2012-239496 A | 12/2012 | |
| JP | 2013-172799 A | 9/2013 | |
| WO | WO-2014013394 A1 * | 1/2014 | ........... A61B 8/4483 |

OTHER PUBLICATIONS

Japanese-language Written Opinion (PCT/ISA/237) issued in PCT Application No. PCT/JP2014/081586 dated Feb. 24, 2015 with English translation (5 pages).

* cited by examiner

F I G. 8

ULTRASOUND PROBE, ELEMENT CIRCUIT THEREOF, AND ULTRASOUND DIAGNOSTIC DEVICE USING SAME

TECHNICAL FIELD

The present invention relates to an ultrasound probe, an element circuit thereof, and an ultrasound diagnostic device using the same and, more particularly, to a technology for miniaturizing an ultrasound probe and an element circuit thereof.

BACKGROUND ART

An ultrasound diagnostic device as well as an X-ray CT device, an MRI device, and the like has been widely used as a device for examining a living organism easily and in real time, and furthermore, its application has been extended into therapeutic support in the fields of puncture examination, contrast agent examination, and the like from conventional diagnostic imaging. Owing to such a background behind the ultrasound diagnostic device, the ultrasound diagnostic device is required to provide images of quality higher than ever before.

For example, Japanese Unexamined Patent Application Publication No. 2004-8535 proposes a therapeutic diagnostic system in which various data used by an ultrasound diagnostic device can be efficiently utilized in external devices without configuring a large-scale therapeutic system.

In addition, Japanese Unexamined Patent Application Publication No. 2012-239496 has already disclosed a technology that improves the symmetric property between the positive voltage output and the negative voltage output by controlling currents injected into transducers using current sources in a pulser circuit, which works as an ultrasound transducer drive device capable of restraining power consumption in the relevant positive voltage supply circuit and negative voltage supply circuit.

PRIOR ART DOCUMENTS

Patent Documents

Patent Document 1: Japanese patent laid-open 2004-8535
Patent Document 2: Japanese patent laid-open 2012-239496

SUMMARY OF INVENTION

Technical Problem

Here, an ultrasound probe that is included in a detection unit of an ultrasound diagnostic device includes a so-called 2-D array IC in which a large number of element circuits, each of which has an transducer and a transmitter for driving the transducer, and the like, are arrayed two-dimensionally, which will be described in detail later. However, in the ultrasound probe of an ultrasound diagnostic device that is required to provide images of higher quality, the miniaturization of transducers is pointed out as a problem, and the fact that the number of the element circuits, which reaches as many as about ten thousand in some cases, leads to the large increase of the size of the relevant 2-D array IC and further leads to the high cost of the ultrasound diagnostic device, is also pointed out as a problem.

The present invention has been achieved in view of the abovementioned problems in mind, and in particular, the present invention can be applied to an ultrasound probe required to provide images of high quality. The present invention provides a technology with the use of which it becomes possible to manufacture a large number of transducers and transmitters for driving the transducers without largely increasing the size of the relevant 2-D array integrated circuit (IC), with the result that the low cost of the ultrasound probe can be realized. To put it more concretely, one of the objects of the present invention is to provide an ultrasound probe and element circuits of the ultrasound probe to which the above technology is applied, and further to provide an ultrasound diagnostic device using the ultrasound probe and the element circuits.

Solution to Problem

In order to attain the above object, the present invention provides an ultrasound probe that includes: a 2-D array transducer including a plurality of transducers which are arrayed two-dimensionally; and a 2-D array IC in which are formed, upon an IC substrate; drive circuits prepared for the transducers on a one-to one basis to drive the transducers of the 2-D array transducer at different timings with prescribed delay quantities respectively; and common current sources which supply drive currents to the transducers of the 2-D array transducer. Here, the number n of the common current sources which are formed upon the IC substrate is fewer than the number N of the drive circuits which are formed upon the IC substrate.

Furthermore, in order to attain the above object, the present invention provides element circuits that are formed on an IC substrate and used for driving transducers of a 2-D array transducer, in which plural transducers are arrayed two-dimensionally, at different timings with prescribed delay quantities respectively. Each of the element circuits includes: a transmitter prepared for each transducer of the 2-D array transducer; a delay control circuit for generating a prescribed delay quantity; and a receiver for receiving a signal from each transducer; and each of the element circuits is connected to a common current source for supplying a driving current to the transducer of the 2-D array transducer. Here, each of the number of transmitters, the number of the delay control circuits, and the number of receivers is equal to the number N of transducers of the 2-D array transducer, and the number n of common current sources is smaller than the number N of the transducers of the 2-D array transducer.

In addition, in order to attain the above object, the present invention provides an ultrasound diagnostic device including a device body having at least a control unit and an ultrasound probe electrically coupled to the device body, where the ultrasound probe includes the ultrasound probe or element circuits described in the above descriptions.

Advantageous Effect of Invention

The above-described present invention can be applied to an ultrasound probe that is required to provide images of higher quality, and makes it possible to manufacture a large number of transducers and transmitters for driving the transducers without largely increasing the size of the relevant 2-D array IC, with the result that an ultrasound probe and element circuits that can be realized at low cost as well as an ultrasound diagnostic device using the above components are provided.

DESCRIPTION OF EMBODIMENTS

An embodiment of the present invention will be described in detail with reference to the accompanying drawings.

Figure 1:
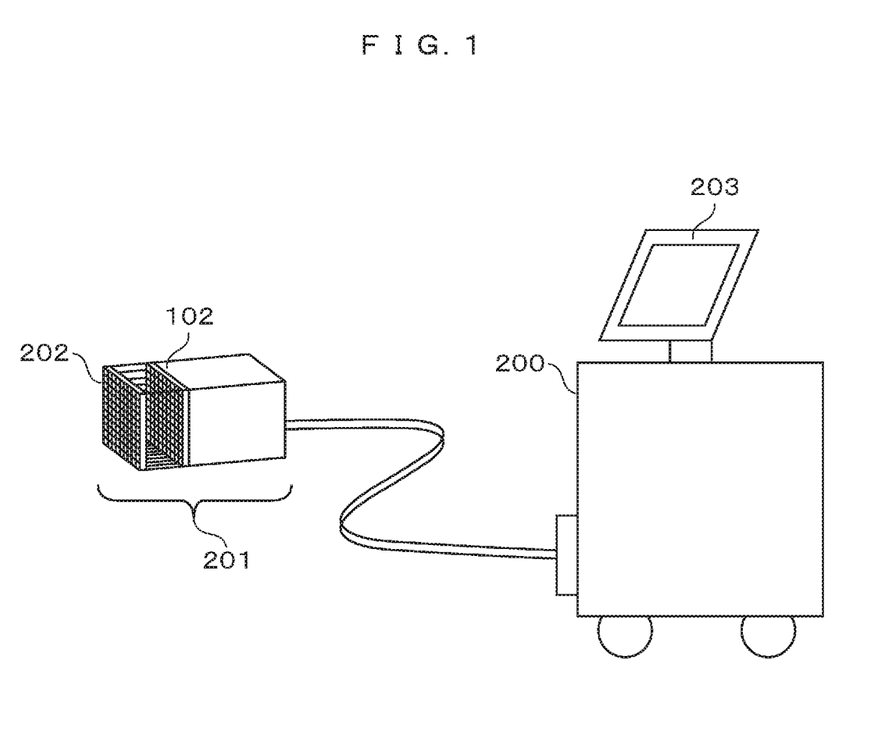
FIG. 1 is a diagram showing the overall structure of an ultrasound diagnostic device according to an embodiment of the present invention.

FIG. 1 shows the overall structure of an ultrasound diagnostic device according to an embodiment of the present invention. As shown in FIG. 1, the ultrasound diagnostic device according to the present invention includes a device body 200 and an ultrasound wave probe 201 that is disposed outside the device body and electrically coupled to the device body via an electrical wire or the like. Furthermore, a CPU (Central Processor Unit) and various memories included in an operation processing unit used for controlling the entirety of the ultrasound diagnostic device or parts of the ultrasound diagnostic device, various power supply circuits, drive circuits that generate drive signals for the ultrasound probe, an image processing circuit that deals with signals from the ultrasound probe, and the like are installed inside the chassis of the device body 200 although they are not diagrammatically shown. In addition, the ultrasound diagnostic device includes an input device including a keyboard, a mouse, and the like, and an output device including, for example, a liquid crystal display 203 although they are also not diagrammatically shown. Here, this device body 200 is configured to be freely movable over the floor by means of casters installed on the bottom of the device body 200.

The ultrasound probe 201, which is disposed outside the device body 200, includes a 2-D array transducer on the surface of which a large number of transducers 202 (for example, the number reaches as many as about ten thousand in some cases) are two-dimensionally (planarly) arrayed, and a 2-D array IC 102 in which a large number of circuits for driving the transducers are two-dimensionally (planarly) arrayed. Here, the circuits are electrically connected to the transducers arrayed two-dimensionally in the 2-D array transducer 202 on a one-to-one basis.

Figure 2:
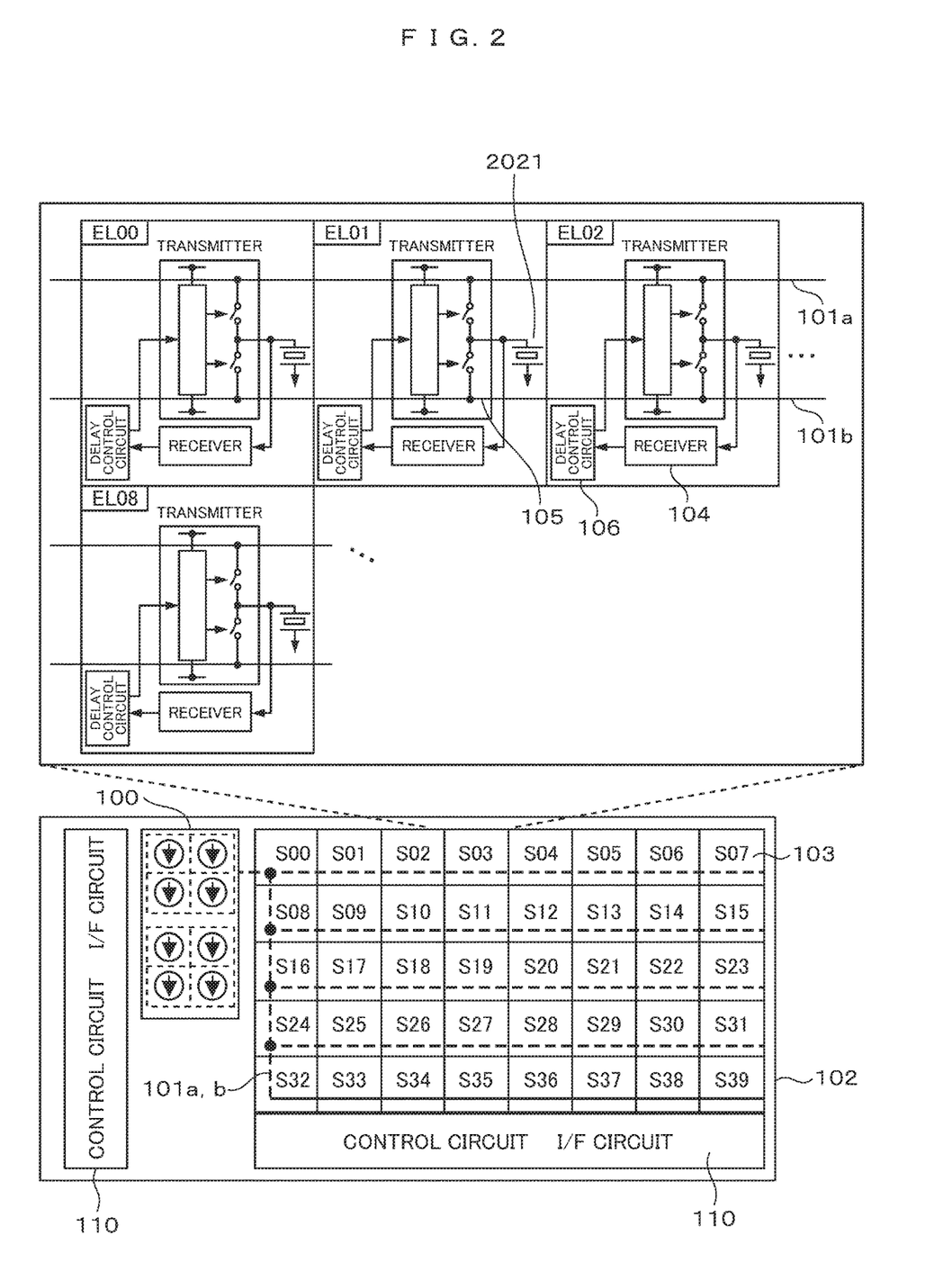
FIG. 2 is a diagram showing the detailed structure of a 2-D array IC of the above ultrasound diagnostic device.

Next, FIG. 2 shows the detailed structure of the abovementioned 2-D array IC 102. As shown in the lower part of FIG. 2, two-dimensionally disposed on a semiconductor substrate in the 2-D array IC 102 are, for example, control circuits, I/F circuits 110 (in this example, two control circuits and two I/F circuits), a common current source unit 100, and plural subarrays 103 (in this example, 40 subarrays in a 5 rows-by-8 columns array, that is, a subarray S00 to a subarray S39). Furthermore, as shown in the upper part of FIG. 2, formed in one of these subarrays S00 to S39 are 64 (=8×8) element circuits (EL00 to EL63. In the upper part of FIG. 2, only some of EL00 to EL63 are shown).

As clearly shown in FIG. 2, each of the element circuits (EL00 to EL63) includes a receiver 104, a transmitter 105, and a delay control circuit 106, and element circuits belonging to the same row (for example, EL00 to EL07) are electrically coupled to the abovementioned common current source unit 100 via a couple of current wires, that is, a couple of a positive current wire 101a and a negative current wire 101b. Here, in FIG. 2, each transducer of the 2-D array transducer 202, which brings in a drive signal from the transmitter 105 and at the same time outputs a reception signal to the receiver 104, is depicted with a reference sign 2021 for purposes of illustration, but in reality each transducer is installed not in the 2-D array IC but in the 2-D array transducer 202 as described before (refer to FIG. 1). In addition, the common current source unit. 100 usually includes high voltage MOS elements as later shown in FIG. 5 as an example. Furthermore, the transmitter 105 includes, for example, a level shift circuit, switching elements, and the like as shown in FIG. 2.

Next, the outline of beam-forming executed by the ultrasound probe 201, the configuration of which has already been explained above, will be described with reference to FIG. 3. As is clear in FIG. 3, drive signals from transmitters 105 are applied at predefined timings respectively to the 2-D array transducer 202 in which plural transducers 2011 are planarly arrayed (refer to waves in FIG. 3). In addition, delay control circuits 106, which generate plural waves with predefined delay quantities respectively (refer to arrows in FIG. 3) after bringing in a signal from external (refer to a wave coming in from the right in FIG. 3) and output these waves to the transmitters 105, are coupled to the input sides of these transmitters 105.

Figure 3:
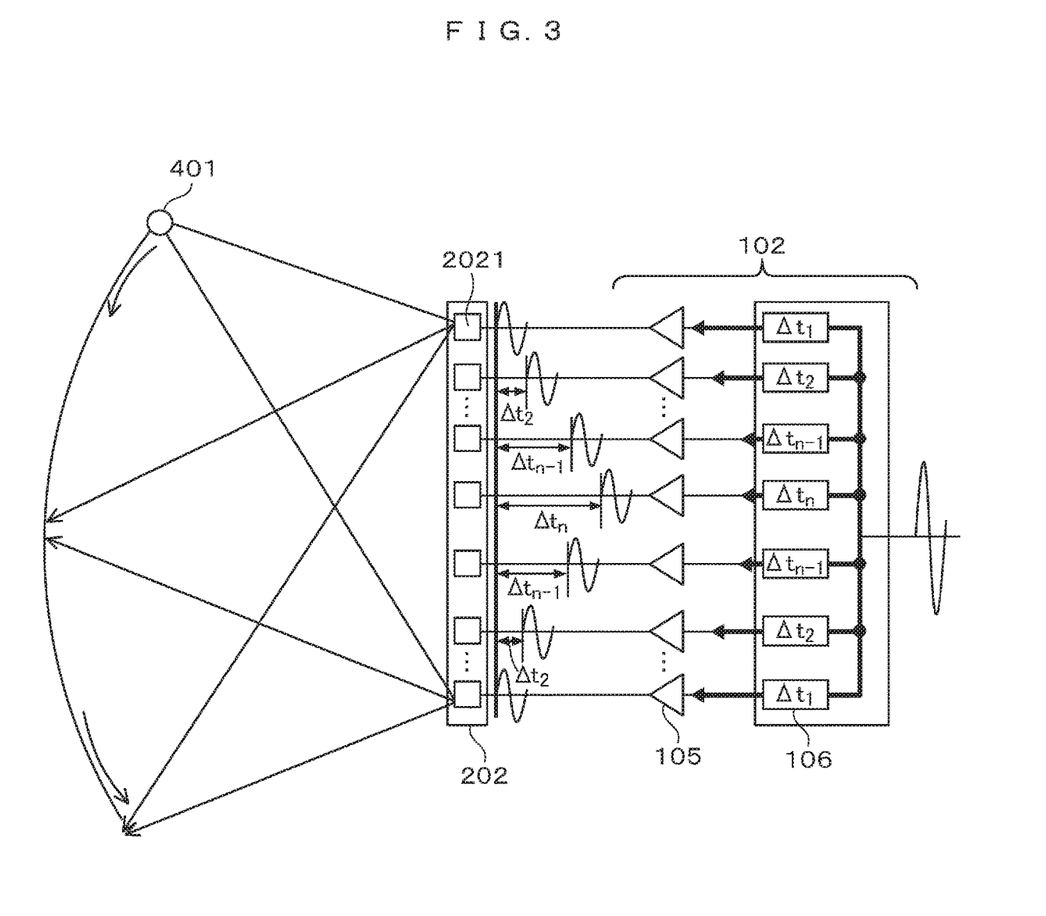
FIG. 3 is a diagram showing the outline of beam-forming executed by an ultrasound probe including the 2-D array IC.

Thanks to such a configuration of the ultrasound probe, a drive timing for driving each transducer 2021 of the 2-D array transducer 202 can be controlled as shown in FIG. 3, and therefore focus points (that is, points at which ultrasounds are overlapped with each other) can be handled. As a result, an image can be generated on the basis of signals obtained by receiving ultrasound waves from individual focus points.

Figure 4:
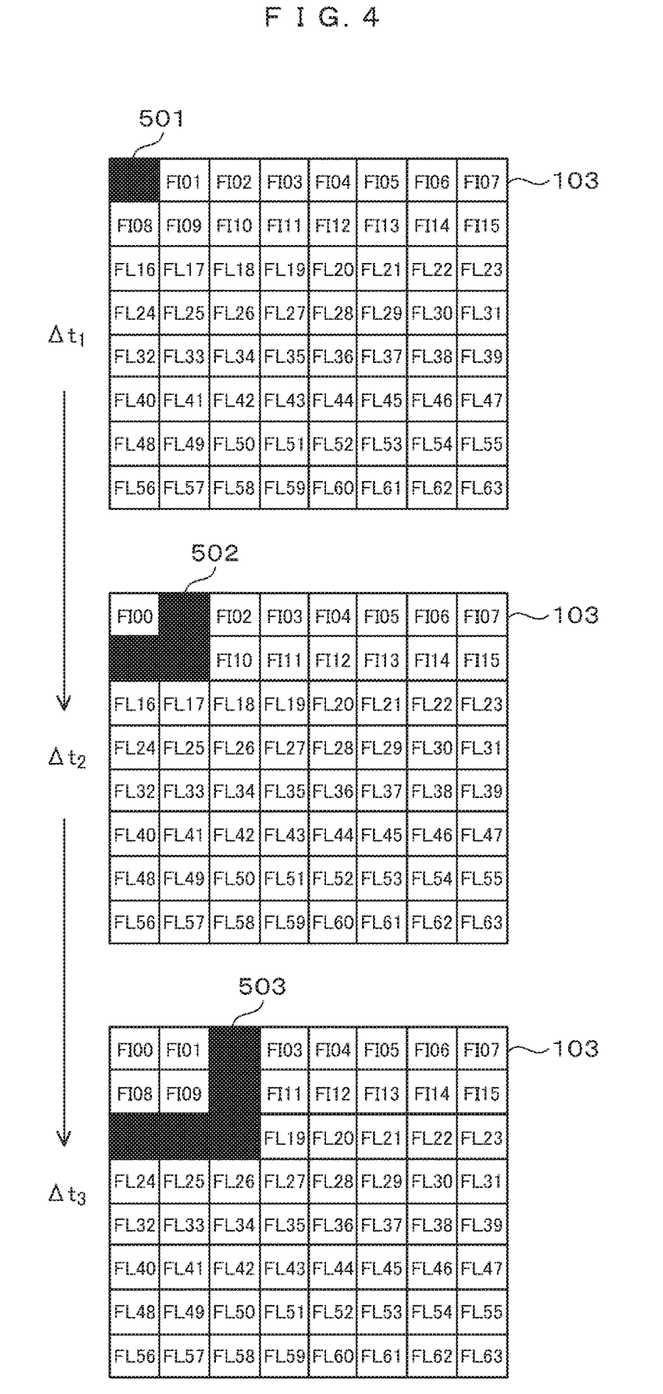
FIG. 4 is a diagram for explaining the operation of the 2-D array IC included in the above ultrasound probe.

In the ultrasound probe, because the delay characteristics of timings at which ultrasound waves are transmitted from the transducers 2021 of the 2-D array transducer 202 are controlled by the delay control circuits 106 respectively as described above, the timings for driving the transducers generated by the element circuits (EL00 to EL63) are different from each other. An example regarding the timings different from each other is shown in FIG. 4, and at the same time the behavior of the example will be explained below.

First, an element circuit (EL00) for driving an transducer at the time Δt1 is denoted by a reference sign 501. Next, element circuits (EL01, ELL08, and EL09) for driving transducers respectively at the time Δt2 are denoted by a reference sign 502. Then, element circuits (EL03, EL10, EL16, EL17, and EL18) for driving transducers respectively at the time Δt3 are denoted by a reference sign 503.

Figure 5:
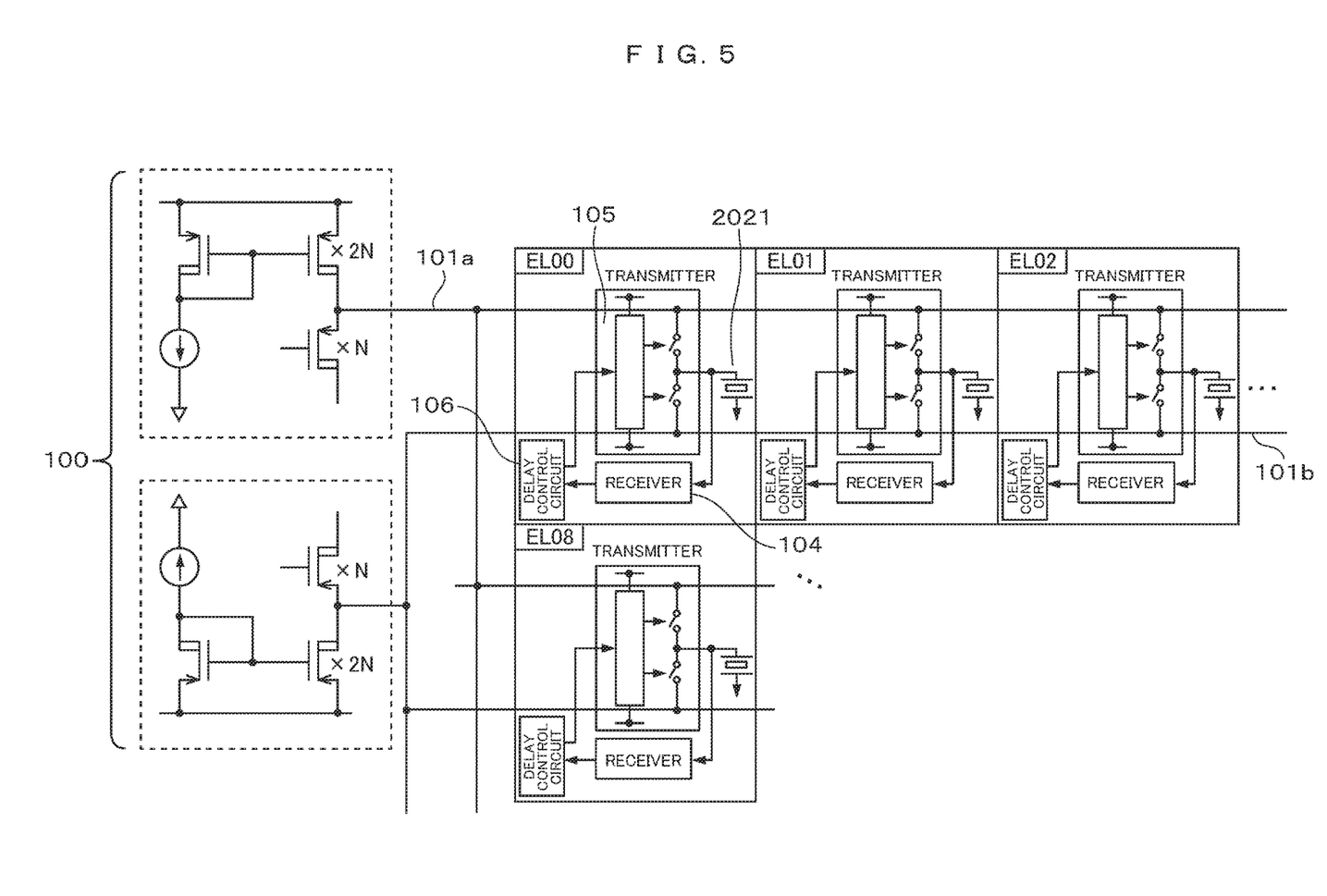
FIG. 5 is a diagram for explaining the operation of the 2-D array IC including common current sources.

At the time Δt1, as shown in FIG. 5, owing to the operation of the element circuit (EL00), a positive current source or a negative current source of the common current source unit 100 supplies a current to a transmitter 105 via the positive current wire 101a or the negative current wire 101b, and a voltage is supplied to an transducer 2021 of the 2-D array transducer, with the result that the transducer 2021 transmits an ultrasound wave. In addition, although not shown in FIG. 5, at the time Δt2, owing to the operations of three element circuits (EL01, EL08, and EL09), positive current sources or negative current sources of the common current source 100 supply currents to transmitters 105 via the positive current wire 101a or the negative current wire 101b, and voltages are supplied to three transducers 2021 of the 2-D array transducer, with the result that the transducers transmit ultrasound waves respectively, and furthermore, at the time Δt3, owing to the operations of five element circuits (EL03, EL10, EL16, EL17, and EL18), the positive current sources or the negative current sources of the common current source 100 supplies currents to transmitters 105 via the positive current wire 101a or the negative current wire 101b, and voltages are applied to five transducers 2021 of the 2-D array transducer, with the result that the transducers transmit ultrasound waves respectively.

As described above, because, in the ultrasound probe according to the present invention, the 2-D array IC 102 for driving the 2-D array transducer 202 is configured to include the individual element circuits (EL00 to EL62), which drive and control the relevant transducers 2021 respectively, and the common current source unit 100, which is installed in common for the transducers, in isolation from these element circuits, it becomes possible to largely reduce the number of the current sources installed in the common current source unit 100 in comparison with a conventional case where current sources are installed for transducers on a one-to-one basis. In particular, because usually a current source unit 100 is comprised of high voltage MOS elements, a current source unit with its structure being conventional occupies the majority of the relevant circuit substrate. In comparison with the current source unit with its structure being conventional, as in the case of the present invention, if current sources are used in common, the number of the current sources can be reduced, which makes it possible to realize the scaling down of the size of the circuit substrate of the relevant IC, and the cost reduction of the relevant ultrasound probe as well.

To put it more concretely, it will be understood that the number of necessary current sources of the common current source unit 100 is the number n of transducers that are driven at the same time among the total number N of the transducers included in the 2-D array transducer 202, that is, the total number of transducers obtained by summing up the numbers of transducers of 64 element circuits (EL00 to EL63) formed in all the 40 subarrays 103 (S00 to S39) formed in the above 2-d array IC (the total number N is 64×40(=2560)) (N>n). Furthermore, in particular, as is the case with the above-mentioned embodiment, if the common current source unit 100 is comprised of positive current sources and negative current sources, and the positive current sources or the negative current sources are selectively used, it will be understood by those skilled in the art that the number of the current sources can be more reduced. Alternatively, although it depends on the characteristics of transducers, it is also possible for the common current source unit 100 to be configured to include only positive current sources or negative current sources.

Figure 6:
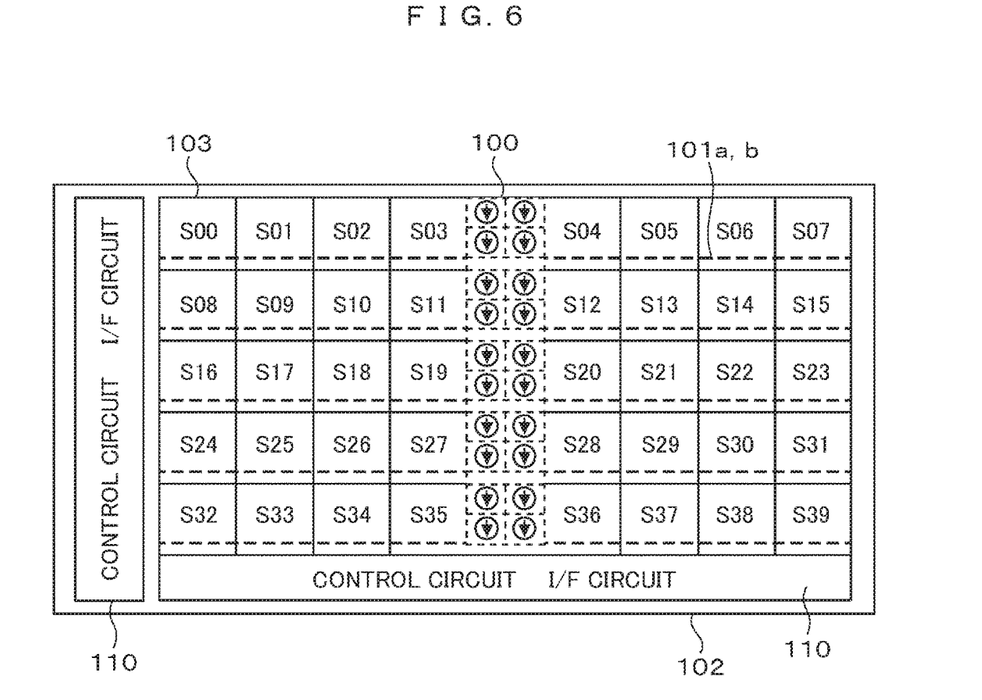
FIG. 6 is a diagram showing a modified example of the above 2-D array IC.

In addition, in the above example, although the common current source unit 100 is formed purposely outside the subarrays 102 in the 2-D array IC 102 as shown in FIG. 2, it is also possible as an alternative that the common current source unit 100 is installed so as to be inserted into the center of the subarrays 103 as shown in FIG. 6. Here, owing to such a circuit configuration as above, distances from the individual subarrays 103 to the common current source unit 100 can be more uniform, and therefore an ultrasound probe of higher transmission quality can be obtained.

Furthermore, the above example has been explained in such a way that timings at which ultrasound waves are transmitted from the transducers 2021 of the 2-D array transducer 202 are gradually spread from the upper left corner (501) of each subarray 103 to the lower right corner as shown in FIG. 4, but the present invention can be applied to not only the above way but also various ways in which ultrasound waves are transmitted at various timings.

Figure 7:
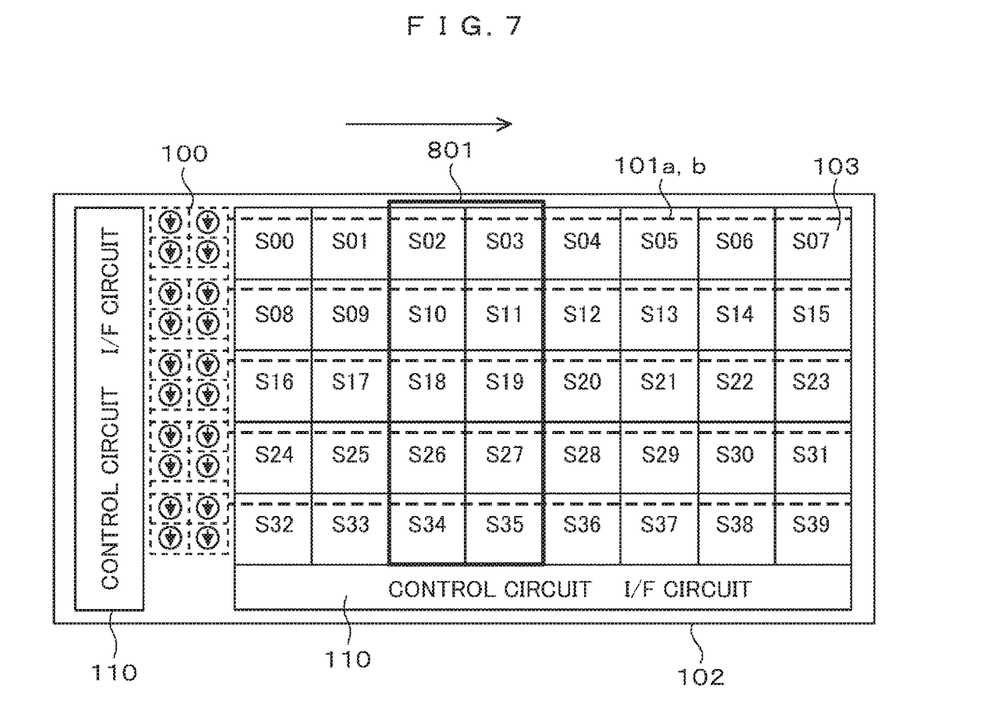
FIG. 7 is a diagram showing another modified example of the above 2-D array IC.

For example, it is possible to configure timings, at which the transducers 2021 of the 2-D transducer 202 are driven, in such a way that an area 801, which is comprised of 10 subarrays 103 (subarrays in a 2 rows-by-5 columns array) being driven at the same time, sequentially moves in a direction shown by an arrow as shown in FIG. 7. In this example, the common current source unit 100 is configured to supply constant currents to 8 subarrays 103 that are disposed row-wise. In this example, it is sufficient that a current source of the common current source unit 100 for each row of the subarrays 103 has a capacity for supplying currents to 2 subarrays 103, that is, to 128 (64×2) element circuits.

Figure 8:
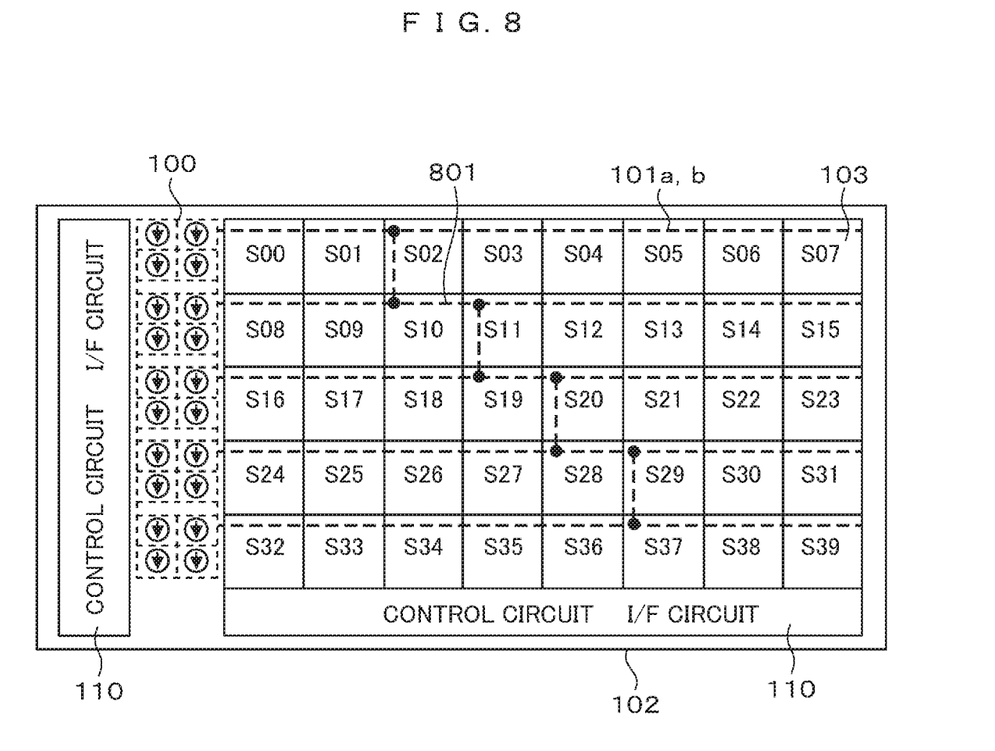
FIG. 8 is also a diagram showing another modified example of the above 2-D array IC.

Alternatively, FIG. 8 shows an example of a simultaneously driven rectangular area 801 that includes 9 subarrays 103 in a 3 rows-by-3 columns array, and sequentially moves. In this case, it is sufficient that a current source for each row has a capacity for supplying currents to 3 subarrays 103, that is, to 192 (64×3) element, circuits.

In the above examples, it has been explained that each current source of the common current source unit 100 supplies currents to plural subarrays disposed in a row direction in order to supply currents to element circuits installed corresponding to transducers 2021 of the 2-D array transducer 202 on a one-to-one basis in units of subarrays 103 (that is, in units 63 element circuits EL00 to EL63). However, the present invention is not limited to the above current supply methods, and it is sufficient that the common current source unit 100 has a capacity large enough to work as a constant current source for transducers or element circuits that are driven simultaneously among all the transducers of the 2-D array transducers 202, that is, all the element circuits of the 2-D array IC 102.

In other words, the ultrasound probe and the element circuits thereof, which have been described in detail, according to the present invention makes it possible to reduce an area occupied by high voltage MOS elements, which occupies a large part of the relevant IC substrate, by integrating current sources conventionally, which are installed for individual transmitters (element circuits) on a one-by-one basis, into a common current source, and by configuring the common current source so as to have a capacity large enough to supply currents consumed by transducers driven simultaneously. Owing to the above configuration of the common current source, the size of the circuit can be reduced, and therefore the low cost of the circuit is realized. In addition, the above configuration makes it possible to couple the common current source unit 100 to transducers mounted on a high density, and therefore an ultrasound diagnostic device that can be made further miniaturized and of higher quality is realized.

Furthermore, the present invention is not limited to the above-described embodiment, and various modification examples can be included in the present invention. For example, the above-described embodiment is made for explaining the entire system of the ultrasound diagnostic device in detail in order to make the present invention easy to understand, and therefore all the components described so far are not always indispensable for the present invention. In addition, a part of the configuration of one embodiment can be replaced with a part of configuration of another embodiment, or a new embodiment may be made by adding a part of the configuration of one embodiment to the configuration of another embodiment. In addition, a new embodiment of the present invention may be made by adding a different configuration to a part of the configuration of each embodiment, deleting a part of the configuration from each embodiment, or replacing a part of configuration of each embodiment with a different configuration. Furthermore, the entireties or parts of the above configurations, functions, processing units, processing means, and the like can be realized by hardware manufactured by, for configurations, functions, and the like can be realized by software provided by a processor's interpreting and executing programs that realize the workings of the above configurations, functions, and the like.

LIST OF REFERENCE SIGNS

200 . . . device body 201 . . . ultrasound probe 2021 . . . transducer 202 . . . 2-D array transducer 100 . . . common current source unit 101a . . . positive current wire 101b . . . negative current wire 102 . . . 2-D array IC 103 . . . subarrays 104 . . . receiver 105 . . . transmitters 106 . . . delay control circuits element circuits . . . EL00-EL63

What is claimed is:

1. An ultrasound probe comprising:
a 2-D array transducer including a plurality of transducers which are arrayed two-dimensionally; and
a 2-D array integrated circuit (IC) in which are formed, upon an IC substrate,
drive circuits prepared for the transducers of the 2-D array transducer on a one-to-one basis to drive the transducers at different timings with prescribed delay quantities respectively, and
common current sources which supply drive currents to the transducers of the 2-D array transducer,
wherein the number n of the common current sources which are formed upon the IC substrate is fewer than the number N of the drive circuits which are formed upon the IC substrate, and
wherein the number n of the common current sources formed upon the IC substrate is set to a number large enough for the common current sources to adequately work as current sources for the driving circuits to drive transducers that are driven at the same timing among the N drive circuits formed on the IC substrate.

2. The ultrasound probe according to claim 1, wherein there are a plurality of transducers that are driven at the same timing, and the number n of the common current sources formed upon the IC substrate is set so that the common current sources can deal with the maximum number of the plurality of the transducers.

3. The ultrasound probe according to claim 2, wherein the numbers of transducers that are driven at different timings respectively are different from each other.

4. The ultrasound probe according to claim 2, wherein the numbers of transducers that are driven at different timings respectively are the same with each other.

5. An element circuit that is formed on an IC substrate and used for driving each of a plurality of transducers of a 2-D array transducer, in which the plurality of transducers are arrayed two-dimensionally, at a different timing from other transducers with a prescribed delay quantity, the element circuit comprising:
a transmitter prepared for each transducer of the 2-D array transducer;
a delay control circuit for generating the prescribed delay quantity;
a receiver for receiving a signal from each transducer; and
a common current source for supplying a driving current to the transducer of the 2-D array transducer,
wherein each of the number of transmitters, the number of delay control circuits, and the number of receivers is equal to the number N of the transducers of the 2-D array transducer, and
the number n of common current sources is smaller than the number N of the transducers of the 2-D array transducer,
wherein the transmitter, the delay control circuit, and the receiver are integratedly formed as a subarray, and the common current source is formed in a region on the IC substrate other than a region in which the subarray is formed, and
wherein the common current source is disposed on the central part of the subarrays on the IC substrate.

6. The element circuit according to claim 5, wherein the common current source is formed by high voltage MOS elements.

7. An ultrasound diagnostic device comprising:
a device body having at least a control unit; and
an ultrasound probe electrically coupled to the device body,
wherein the ultrasound probe includes the ultrasound probe described in claim 1.

8. An ultrasound diagnostic device comprising:
a device body having at least a control unit; and
an ultrasound probe electrically coupled to the device body,
wherein the ultrasound probe includes the element circuit described in claim 5.

* * * * *